(12) United States Patent
Gollier et al.

(10) Patent No.: US 7,454,094 B2
(45) Date of Patent: Nov. 18, 2008

(54) OPTICAL READER SYSTEM AND METHOD THAT USES NON-COHERENT ILLUMINATION AND ANGULAR FILTERING TO INTERROGATE A LABEL INDEPENDENT BIOSENSOR

(75) Inventors: Jacques Gollier, Painted Post, NY (US); Gordon M. Shedd, Lawrenceville, PA (US)

(73) Assignee: Corning Incorporated, Corning, NY (US)

( * ) Notice: Subject to any disclaimer, the term of this patent is extended or adjusted under 35 U.S.C. 154(b) by 96 days.

(21) Appl. No.: 11/213,654

(22) Filed: Aug. 26, 2005

(65) Prior Publication Data
US 2006/0182382 A1  Aug. 17, 2006

Related U.S. Application Data

(63) Continuation-in-part of application No. 11/058,155, filed on Feb. 14, 2005, now Pat. No. 7,346,233.

(51) Int. Cl.
- G02B 6/26 (2006.01)
- G01J 3/28 (2006.01)
- C12M 1/34 (2006.01)

(52) U.S. Cl. .............. 385/12; 385/27; 385/33; 385/37; 356/128; 356/300; 356/326; 356/328; 435/287.1

(58) Field of Classification Search ............... 385/12, 385/27, 33, 37; 356/128, 300, 326, 328; 435/287.1
See application file for complete search history.

(56) References Cited

U.S. PATENT DOCUMENTS

| 4,815,843 | A | 3/1989 | Tiefenthaler et al. ......... 356/128 |
| 5,396,325 | A | 3/1995 | Carome et al. .............. 356/128 |
| 2002/0009812 | A1 | 1/2002 | Miura et al. ................. 436/518 |
| 2002/0127565 | A1 | 9/2002 | Cunningham et al. .......... 435/6 |
| 2002/0168295 | A1 | 11/2002 | Cunningham et al. ..... 422/82.05 |
| 2003/0017580 | A1 | 1/2003 | Cunningham et al. ..... 435/287.2 |
| 2003/0017581 | A1 | 1/2003 | Li et al. ................... 435/287.2 |
| 2003/0026891 | A1 | 2/2003 | Qiu et al. ....................... 427/58 |

(Continued)

FOREIGN PATENT DOCUMENTS

DE  43 05 830  8/1994

(Continued)

OTHER PUBLICATIONS

M. Wiki et al., "Novel integrated optical sensor based on a grating coupler triplet", Biosensors & Bioelectronics, vol. 13, 1998, pp. 1181-1185.

(Continued)

*Primary Examiner*—Frank G Font
*Assistant Examiner*—Michael P Mooney
(74) *Attorney, Agent, or Firm*—William J. Tucker, Esq; Thomas R. Beall

(57) ABSTRACT

An optical reader system and method are described herein that directs a non-coherent light towards a biosensor, collects the non-coherent light which is reflected (or transmitted) from (or through) the biosensor, and then angularly filters the collected non-coherent light to obtain a narrow spectral response which can be analyzed to determine if a biological substance is located on the biosensor or if a biomolecular event took place on the biosensor.

17 Claims, 11 Drawing Sheets

U.S. PATENT DOCUMENTS

| | | | |
|---|---|---|---|
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0035352 A1* | 2/2003 | Worthington | 369/47.35 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0132172 A1 | 7/2004 | Cunningham et al. | 435/287.2 |
| 2004/0132214 A1 | 7/2004 | Lin et al. | 436/518 |
| 2004/0145752 A1 | 7/2004 | Angeley | 356/521 |
| 2004/0151626 A1 | 8/2004 | Cunningham et al. | 422/58 |
| 2004/0223881 A1 | 11/2004 | Cunningham et al. | 422/82.05 |
| 2005/0070027 A1 | 3/2005 | Gollier et al. | 436/518 |

FOREIGN PATENT DOCUMENTS

| | | |
|---|---|---|
| EP | 1 239 279 | 9/2002 |
| WO | 94/25850 | 11/1994 |

OTHER PUBLICATIONS

M. Wiki et al., "Wavelength-interrogated optical sensor for biochemical applications", Optics Letters, Apr. 1, 2000, vol. 25, No. 7, pp. 463-465.

K. Cottier et al., "Label-free highly sensitive detection of (small) molecules by wavelength interrogation of integrated optical chips", Sensors and Actuators B, vol. 91, 2003, pp. 241-251.

F. Lemarchand et al., "Study of the resonant behaviour of waveguide gratings: increasing the angular tolerance of guided-mode filters", J. Opt. A: Pure Appl. Opt. 1, 1999, pp. 545-551.

D.K. Jacob et al., "Normally incident resonant grating reflection filters for efficient narrow-band spectral filtering of finite beams", J. Opt. Soc. Am. A, vol. 18, No. 9, Sep. 2001, pp. 2109-2120.

F. Lemarchand et al., "Increasing the angular tolerance of resonant grating filters with doubly periodic structures", Optics Letters, Aug. 1, 1998, vol. 23, No. 15, pp. 1149-1151.

* cited by examiner

\* X axis is wavelength (nm)
Y axis is resonant intensity (counts)

US 7,454,094 B2

OPTICAL READER SYSTEM AND METHOD THAT USES NON-COHERENT ILLUMINATION AND ANGULAR FILTERING TO INTERROGATE A LABEL INDEPENDENT BIOSENSOR

CROSS REFERENCE TO RELATED APPLICATION

This application is a continuation-in-part application of U.S. patent application Ser. No. 11/058,155, filed Feb. 14, 2005, now U.S. Pat. No. 7,346,233. The contents of this patent application are incorporated by reference herein.

BACKGROUND OF THE INVENTION

1. Field of the Invention

The present invention relates to an optical reader system and method that directs a non-coherent light towards a biosensor, collects the non-coherent light which is reflected (or transmitted) from (or through) the biosensor, and then angularly filters the collected non-coherent light to obtain a narrow spectral response which can be analyzed to determine if a biological substance is located on the biosensor or if a biomolecular event took place on the biosensor.

2. Description of Related Art

Many areas of biological research today utilize optical non-contact sensor technology to help perform sensitive and time-constrained assays. In such assays, an optical reader system is often used to monitor variations in an optical response of an optical sensor (biosensor) as a biological substance is brought into a sensing region of the biosensor. The presence of the biological substance alters the optical response of the biosensor when it causes a bio-chemical interaction like material binding, adsorption etc . . . This alteration of the optical response enables one to directly monitor biological events in label-free assays where the expense and experimental perturbations of fluorescent dyes are completely avoided.

To directly monitor biological events on the biosensor, the optical reader system needs to use a launch system to launch a light towards the biosensor. And, the optical reader system also needs to use a receive system to receive the light output from the biosensor. The selection of components used in the launch and receive systems like the light source (punctual light source or spatially non-coherent light source) and optical fibers (single mode optical fibers or multimode optical fibers) has a big impact on the performance of the optical reader system. It is a purpose of the present invention to discuss some of the different components that can be used in a launch system and a receive system of a multimode based optical reader system.

BRIEF DESCRIPTION OF THE INVENTION

The present invention includes an optical reader system that has an optical configuration which enables the spectral interrogation of a grating coupled waveguide biosensor. In the present invention, the biosensor is illuminated with white light and with multiple incidence angles. Then, the light that is reflected (or transmitted) by the biosensor is collected and angularly filtered so as to obtain a narrow spectral resonance. The narrow spectral resonance is analyzed to determine if a biological substance is located on the biosensor or if a biomolecular event took place on the biosensor. In one embodiment, the optical reader system uses a multimode fiber which is connected to a spatially non coherent source to illuminate the biosensor. And, then a single mode fiber is used to collect and angularly filter the light beam that is reflected (or transmitted) by the biosensor. Two other embodiments of the optical reader system are also described herein.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
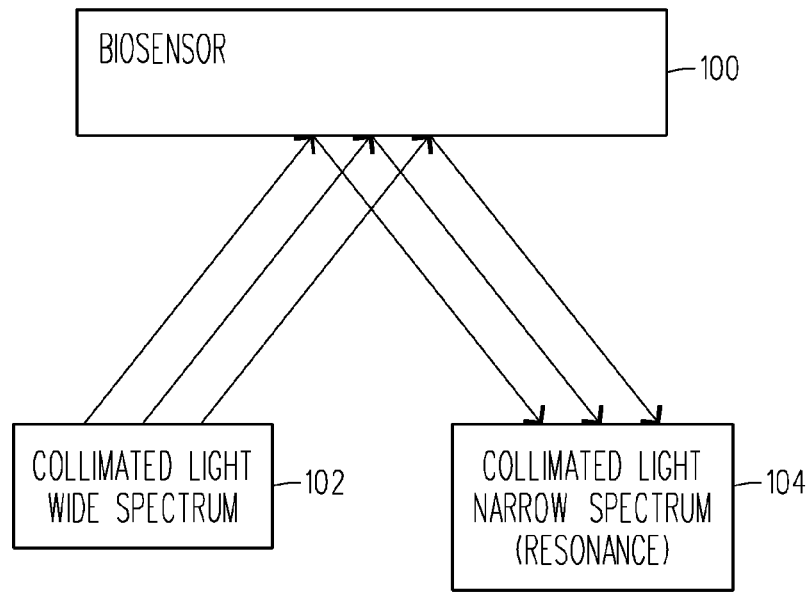
FIG. 1 is a diagram that illustrates the most common optical configuration used today to interrogate a biosensor with a wavelength interrogation configuration.

Prior to describing the different components in the various optical reader systems of the present invention, a brief discussion is provided about the structure and functionality of a biosensor (e.g., resonant grating coupled waveguide (RGW) sensor). And, then a brief discussion is provided about several other types of optical reader systems that can and cannot be used to interrogate a biosensor. Basically, the biosensor has a top surface on which a biological substance (e.g., molecules, proteins) and bulk fluids (cover medium) are deposited. The presence of this biological substance or a biological binding event that is caused by the presence of the biological substance alters the index of refraction at the top surface of the biosensor. And, by probing the biosensor and in particular it's diffraction grating with an optical beam, one can detect this change (~1 part per million) in the refractive index. In this way, the biosensor can be used to detect a wide variety of biological substances or biomolecular binding events (e.g., binding of a drug to a protein). For a more detailed discussion about the structure and functionality of the RWG biosensor 100, reference is made to the following document:

U.S. Pat. No. 4,815,843 entitled "Optical Sensor for Selective Detection of Substances and/or for the Detection of Refractive Index Changes in Gaseous, Liquid, Solid and Porous Samples".

The contents of this document are incorporated by reference herein.

One method that can be used to interrogate the biosensor is known as spectral interrogation. Spectral interrogation entails: (1) illuminating the biosensor at a given incidence angle θ with a multi-wavelength or broadband beam of light; (2) collecting the light reflected (or transmitted) from (or through) the biosensor; and (3) analyzing the spectrum of the collected light with a spectral dispersing device such as a spectrometer. If a biological substance is present or a biomolecular binding event occurs on the top surface of the biosensor, then there is a slight shift in the resonance wavelength. The amount this resonance shift takes place can be seen in the following equation:

$$\lambda = \Lambda(n_{\mathit{eff}} - \sin\theta)$$

were

λ is the resonance wavelength;

Λ is the period of the biosensor's diffraction grating;

θ is the angle of the incident optical beam; and $n_{\mathit{eff}}$ is the effective index of the biosensor's waveguide.

In accordance with this equation, when a biological substance is present or a biomolecular binding event occurs at the surface of the biosensor, the effective refractive index $n_{\mathit{eff}}$ changes. In turn, this causes a variation of the resonance wavelength λ. It is this variation in the resonance wavelength λ that can be monitored so one can detect the presence of the biological substance or the biomolecular binding event.

An important thing to understand from this equation is that in the past it caused one to interrogate the biosensor with a beam that had one single angle in order to obtain a narrow spectral resonance wavelength λ. This meant that one needed to use a well collimated light beam (see U.S. Patent Application No. US 2003/0032039). Because, if one used a non-collimated light beam, then multiple angles would be sent and each angle would excite a different resonance wavelength, which would result in a global increase of the spectral width.

The present invention solves this problem by introducing an optical reader system that can use a non-collimated light beam to interrogate the biosensor. But, before the new optical reader system is described a brief discussion is provided about some of the other types of optical reader systems that can and cannot be used to interrogate a biosensor.

Figure 2:
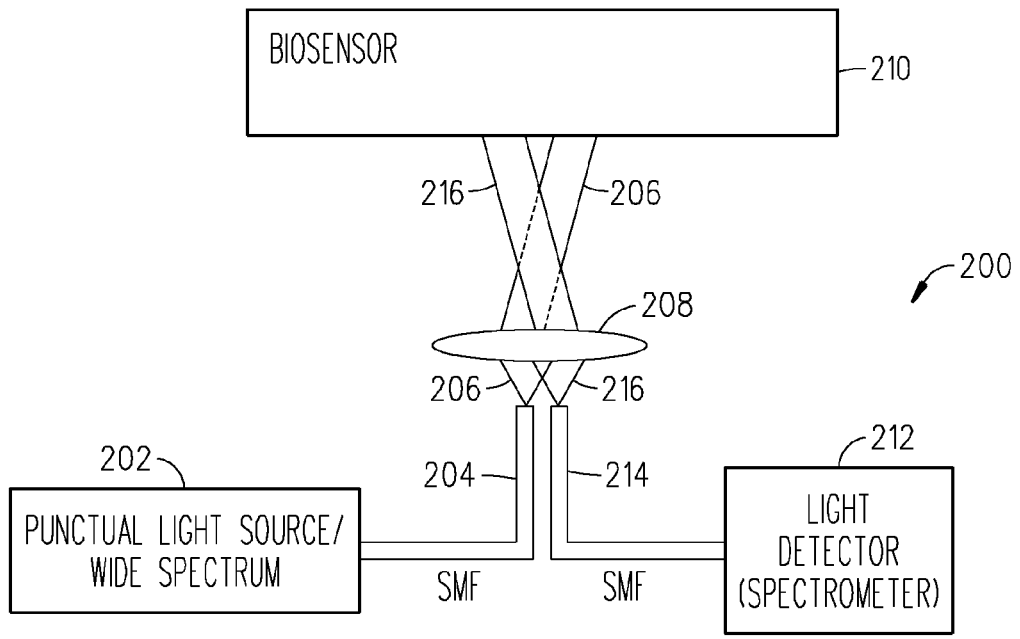
FIG. 2 is a block diagram that illustrates an optical reader system that can be used to implement the optical configuration shown in FIG. 1.

The most common optical configuration used today to interrogate a biosensor 100 is shown in FIG. 1. In this configuration, the interrogation is done by directing a collimated light beam 102 at one single incidence angle θ towards the biosensor 100 and then measuring the wavelength of the reflected light 104. One example of an optical reader system 200 that uses this optical configuration is shown in FIG. 2. As can be seen, the optical reader system 200 has a light source 202 (punctual light source/wide spectrum 202) and a first single mode fiber 204 which emits a light beam 206 through a collimating lens 208 towards the biosensor 210. The optical reader system 200 also has a light detector 212 (e.g., spectrometer 212) which receives a light beam 216 that passed through the collimating lens 208 and a second single mode fiber 214 after being reflected from the biosensor 210. This type of optical reader system 200 was disclosed in co-pending U.S. patent application Ser. No. 11/058,155 entitled "Single Mode (SM) Fiber Optical Reader System and Method for Interrogating Resonant Waveguide-Grating Sensor(s)". The contents of this document are incorporated by reference herein.

The optical reader system 200 presents a lot of advantages, but it has one drawback in that the angular tolerance between it and the biosensor 210 is limited to a few mRd. As a result, this type of configuration is more compatible with a biosensor 210 that has a glass substrate because the glass substrate has a relatively low angular deformation. Unfortunately, this type of configuration is not that compatible with a biosensor 210 which has an injection molded plastic substrate because the plastic substrate has much higher angular deformations.

Figure 3:
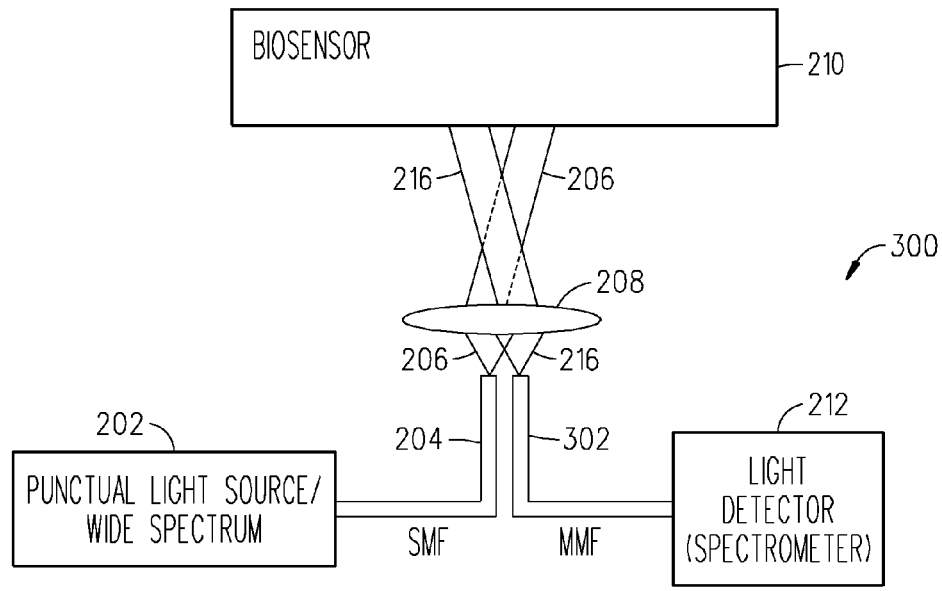
FIG. 3 is a block diagram that illustrates an optical reader system that can not be used to implement the optical configuration shown in FIG. 1.
Figure 4:
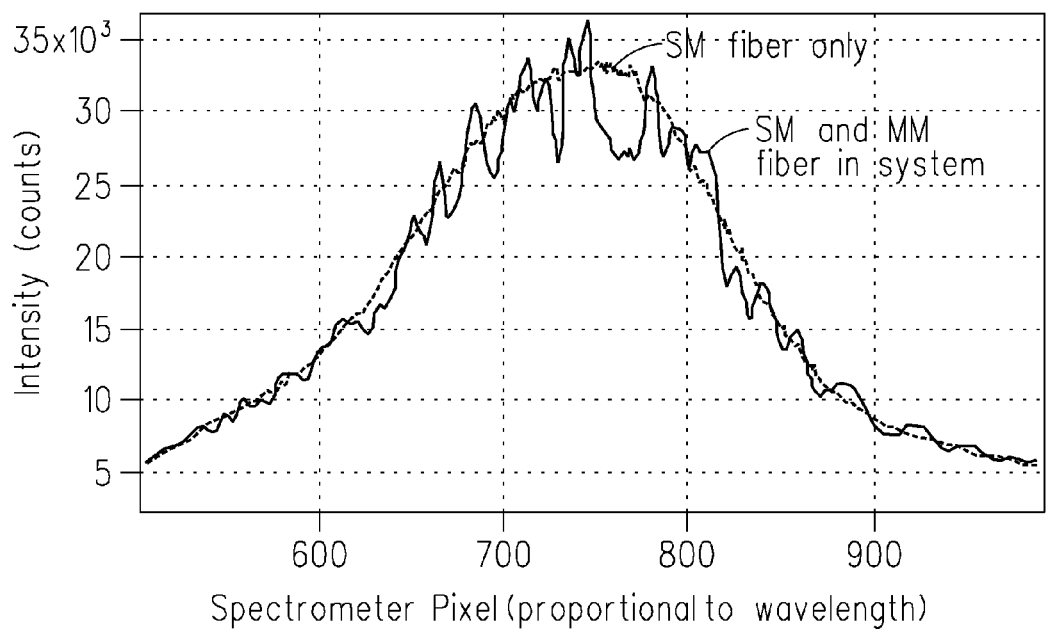
FIG. 4 is a graph which is used to help describe why the optical reader system shown in FIG. 3 can not be used to implement the optical configuration shown in FIG. 1.

One possibility to increase this angular tolerance, is to use an optical reader system 300 as shown in FIG. 3. The optical reader system 300 is the same as optical reader system 200 except that a multimode fiber 302 is used instead of a single mode fiber 214 to collect the light beam 216 reflected from the biosensor 210. Indeed, by using a multimode fiber 302 with a core diameter of 50 microns or more instead of a single mode fiber 214 with a core diameter in the range of 5 microns, the angular tolerance can be relaxed by at least a factor of 10. However, a new problem then occurs because the spectrometer 212 is not necessarily compatible with the use of a multimode fiber 302. This problem occurs because there are a lot of modes that are propagated into the multimode fiber 302 which generates interference that makes the illumination pattern output from the multimode fiber 302 very noisy. As a result, when a multimode fiber 302 is connected to a spectrometer 212, one usually gets a very noisy and unstable spectra. FIG. 4 illustrates this problem by showing a spectrum that was measured when a wide spectrum light source was respectively connected to a single mode fiber and a multimode fiber, where both fibers were put at the entrance of a spectrometer.

Figure 5:
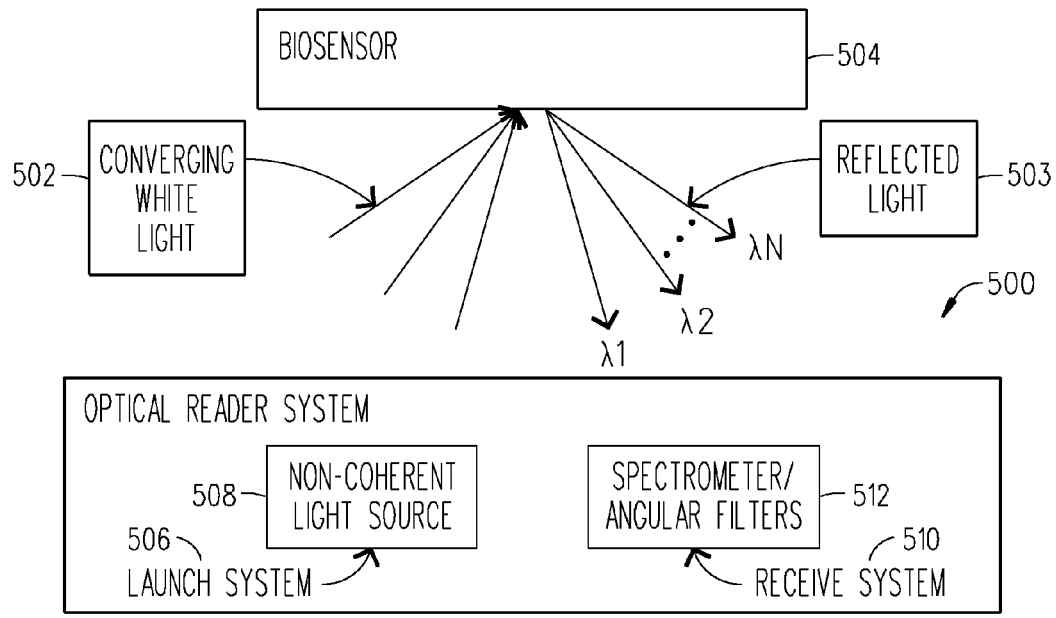
FIG. 5 is a diagram that illustrates an optical configuration that is used by the optical reader systems of the present invention.

So, using optical reader system 300 is not an option to increase the angular tolerance. However, the optical reader system 500 made in accordance with the present invention solves this angular tolerance problem. As shown in FIG. 5, the optical reader system 500 which is described in greater detail below involves the use of a non-collimated light beam 502 to interrogate a biosensor 504. As can be seen, when a launch system 506 uses a non-coherent light source 508 to emit the non-collimated white light beam 502 towards the biosensor 504, then multiple wavelengths $\lambda_1, \lambda_2 \ldots \lambda_n$ of light 503 are reflected from the biosensor 504 and each wavelength of the reflected light 503 has a specific angle. As discussed in FIG. 3, this was a problem in the past because when all of the light 216 that is reflected by the biosensor 210 is received by a spectrometer 212 then the received light 216 had a very wide resonance which made it unstable for detecting a biological substance or a biological monitoring event.

The optical reader system 500 of the present invention solves this problem by using a receive system 510 which collects the reflected light 503 and angularly filters the collected light 503 such that only one specific angle would be detected by a spectrometer 512. By collecting only one angle $\lambda_2$ (for example) of the reflected light 503, the receive system 510 strongly reduces the spectral width of the resonance wavelength. Two exemplary optical reader systems 500a and 500b that use white non-collimated light 502 for illumination and then angular filter the reflected light 503 are described in detail below with respect to FIGS. 6-7.

Figure 6:
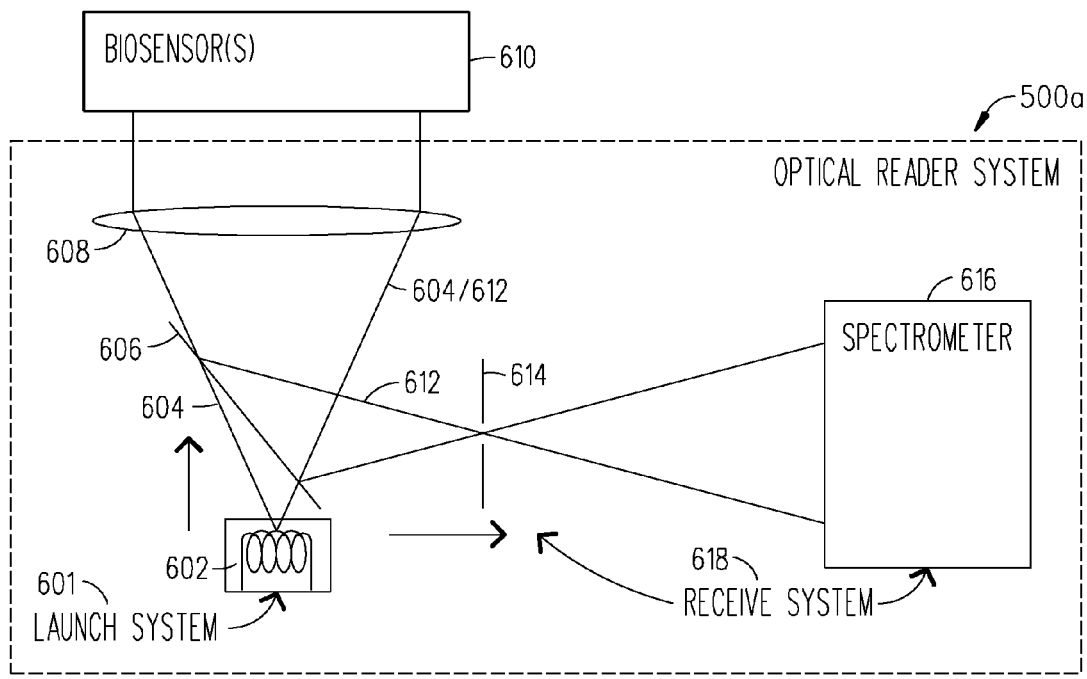
FIG. 6 is a block diagram that illustrates the basic components of an optical reader system in accordance with a first embodiment of the present invention.

Referring to FIG. 6, there is illustrated a diagram of an optical reader system 500a in accordance with the first embodiment of the present invention. The optical reader system 500a has a free beam propagating configuration with a launch system 601 were a lamp 602 (e.g., Quartz Tungsten Halogen (QTH) lamp 602) emits non-coherent light 604 through a beamsplitter 606 and a collimating lens 608 towards one or more biosensors 610. In one embodiment, the biosensors 610 are located within the wells of a microplate (sensor plate). The beam 612 output by the biosensor(s) 610 passes through the collimating lens 608 and is reflected by the beamsplitter 606 and then re-imaged on a slit 614 that effectively angularly filters the collected light beam 612. The angularly filtered light beam 612 is then detected by the spectrometer 616 in the receive system 618. The receive system 618 uses a processor (not shown) to measure the resonance wavelength in the detected angularly filtered light beam 612. Again, it is a change in this resonance wavelength that indicates if a biological substance is located on the biosensor 610 or if a biomolecular event took place on the biosensor 610. It should be appreciated that at the output of the collimating lens 608, the beam 604 is in fact diverging. This happens because a non-coherent extended source 602 like a filament (as shown) is used such that one gets multiple emitting points, each of which emits at a different angle from the output of the collimating lens 608. The divergence of the beam 604 is a function of the focal length of the collimating lens 608 and the size of the light source 602.

Numerically, one can, for instance make an optical reader system 500a that uses a 4×4 mm QTH lamp 602 and a collimating lens 608 which has a focal length of 100 mm. In this case, the divergence of the light beam 604 on the biosensor(s) 610 is 40 mRd which means that the spectral width of the reflected beam 612 is going to be 20 nm assuming the biosensor 610 has a 500 nm grating period. And, by using a 0.1 mm width slit 614 to filter the reflected light beam 612, the spectral width of the resonance can be reduced from 20 nm to 0.5 nm (in first approximation).

Figure 7:
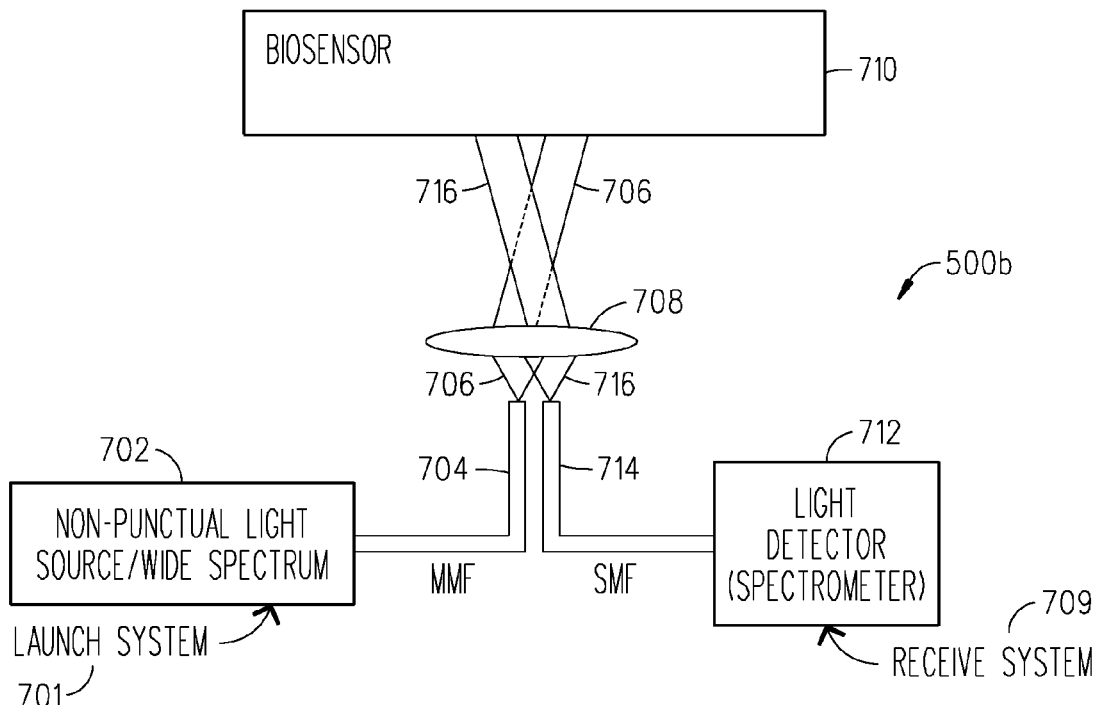
FIG. 7 is a block diagram that illustrates the basic components of an optical reader system in accordance with a second embodiment of the present invention.

Referring to FIG. 7, there is illustrated a diagram of an optical reader system 500b in accordance with the second embodiment of the present invention. The optical reader system 500b has a launch system 701 with a light source 702 (non-punctual light source/wide spectrum 702), a multimode fiber 704 and a collimating lens 708 that function to emit a non-coherent light beam 706 towards the biosensor 710. The optical reader system 500b also has a receive system 709 which includes a light detector 712 (e.g., spectrometer 712) that receives a light beam 716 which passed through the collimating lens 708 and a single mode fiber 714 after being reflected from the biosensor 710. The receive system 709 uses a processor (not shown) to measure the resonance wavelength in the detected angularly filtered light beam 716. Again, it is a change in this resonance wavelength that indicates if a biological substance is located on the biosensor 710 or if a biomolecular event took place on the biosensor 710.

Figure 8:
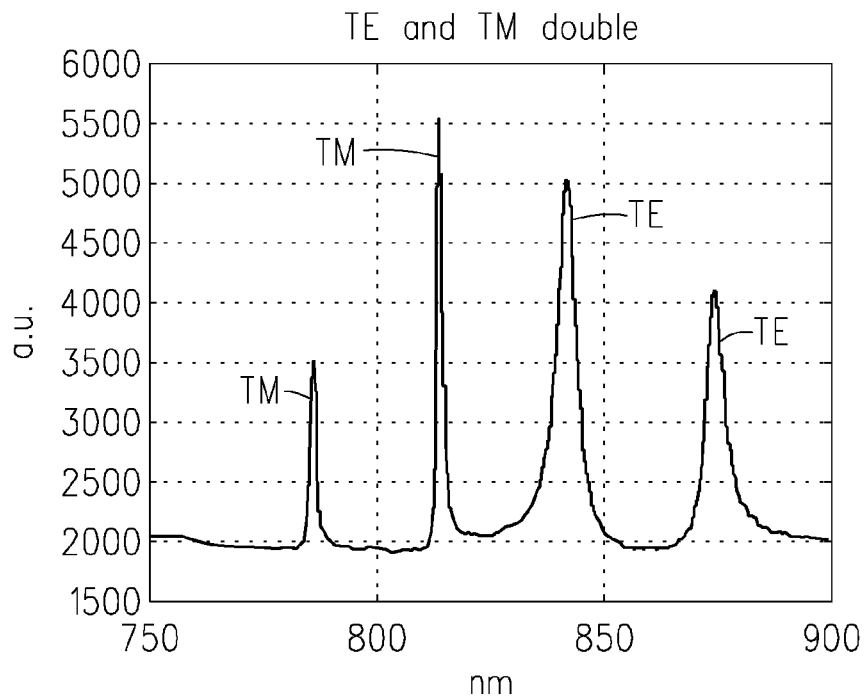
FIG. 8 is a graph that shows a resonance that was obtained while testing the optical reader system shown in FIG. 7.

To test this configuration, an exemplary optical reader system 500b was made where the collimating lens 708 had a focal length of 2.5 mm and the multimode fiber 704 had a core diameter of 0.1 mm. In this case, the divergence of the illuminating beam 706 was 40 mRd which means that; without angular filtering, the spectral width of the resonance would be around 20 nm. However, when angular filtering is provided by the single mode fiber 714 which in this test happened to have a 5 microns core diameter. Then, the single mode fiber 714 would have an angular acceptance cone of 2 mRd which means that the spectral width of the resonance would be expected to decrease from 20 nm to 1 nm (in first approximation). It should be noted that when using the optical reader system 500b, it is particularly important to choose the multimode fiber 704 in such a way that the irradiance level in the fiber core is as homogeneous as possible. As such, a step index multimode fiber 704 is preferred over a gradient index multimode fiber 704. FIG. 8 illustrates a graph that shows the typical resonance which was obtained while testing the exemplary optical reader system 500b. As expected, the resonance width of the TM mode is close to 1 nm. And, for the TE mode, a much wider resonance was detected because the width was dominated by the spectral response of the biosensor 710 itself and not by the efficiency of the angular filtering of the single mode fiber 714. Reference is made to the aforementioned co-pending U.S. patent application Ser. No. 11/058,155, for an additional discussion about the optical reader system 500b and how it compares with and tests against the optical reader system 200 shown in FIG. 2.

When using the optical reader system 500b, particular attention should be made in selecting the wide spectrum light source 702. Because, if a spatially coherent light source such as a nearly punctual source is selected, then mode interferences will be generated in the launch fiber 704. The consequence of these mode interferences is that the angular energy distribution of the illuminating beam 706 is going to be very noisy and unstable resulting in a very noisy resonance wavelength. This problem can be seen in the photo and graph respectively shown in FIGS. 9 and 10.

Figure 9:
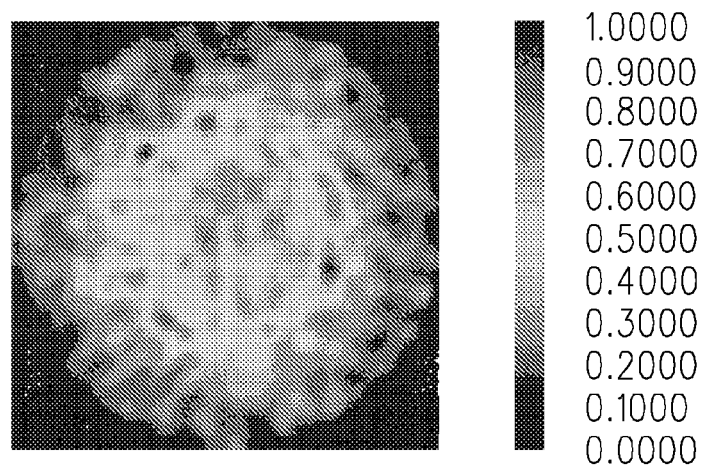
FIG. 9 is a photo that illustrates a problem that occurs when a punctual light source is used in the optical reader system shown in FIG. 7.

FIG. 9 is a photo that shows the typical energy distribution within a 100 micron diameter fiber core of a step index multimode fiber 704 that was measured when using a punctual light source. As can be seen, in the irradiance profile shown on the photo, one gets a very non-homogeneous and noisy power distribution. The shape of this distribution is a function of several factors: (1) the wavelength of the light; (2) the position of the light source on the core of the multimode fiber; and (3) the bending of the multimode fiber.

Figure 10:
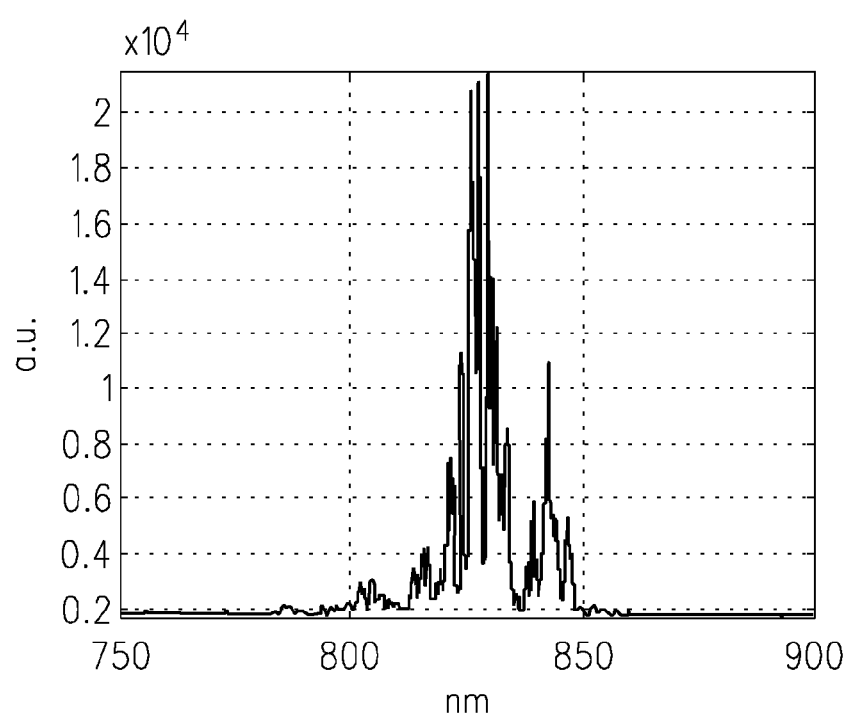
FIG. 10 is a graph that illustrates a typical resonance spectrum that was obtained when a punctual light source was used in the optical reader system shown in FIG. 7.

And, FIG. 10 is a graph that shows the typical resonance spectrum that was obtained when the optical reader system 500b utilized a punctual super luminescent diode as the light source 702. As can be seen, a very noisy spectrum was obtained which happened to rapidly change when the multimode fiber 704 was moved.

Figure 11:
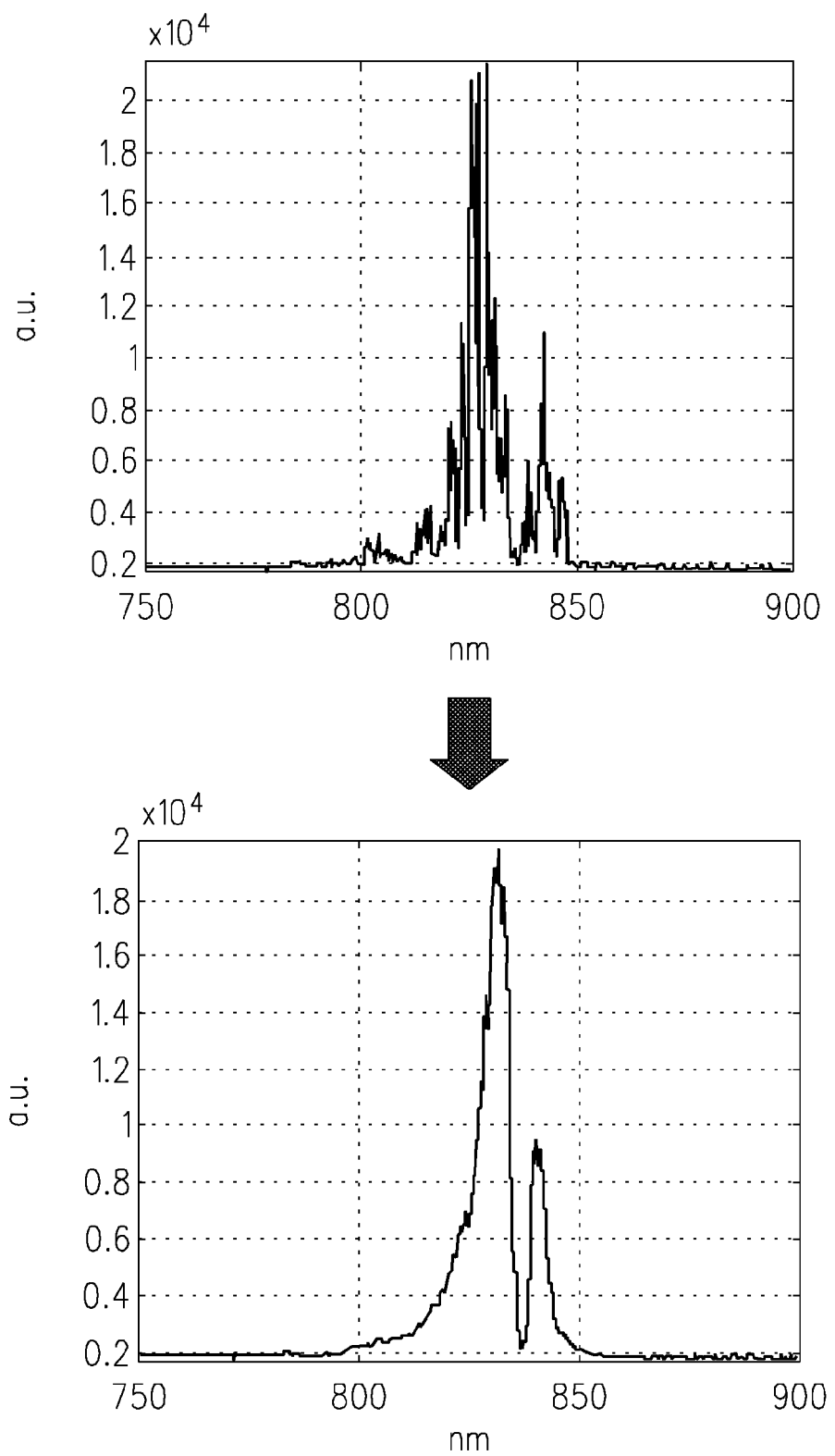
FIG. 11 shows two graphs that are used to illustrate how a spectrum profile can be improved when a static mode scrambler or a dynamic mode scrambler is used in the optical reader system shown in FIG. 7.

One way to partly solve this interference problem, is to use a static mode scrambler or a dynamic mode scrambler. FIG. 11 shows two graphs which illustrate the effect that mode scrambling has on the spectrum profile. As can be seen in the right graph, the noise is highly reduced but one can still observe some unstable fluctuations in the spectrum.

Another more efficient way to solve this interference problem, is to excite as many modes as possible in the multimode fiber 704. This can be achieved by imaging a spatially extended light source 702 such as a QTH lamp or arc lamp on the entrance of the multimode fiber 704. Referring again to FIG. 8, it can be seen that the spectrum that is acquired using an arc lamp as the light source 702 indicates that it is possible to remove the fluctuations using this technique.

Figure 12:
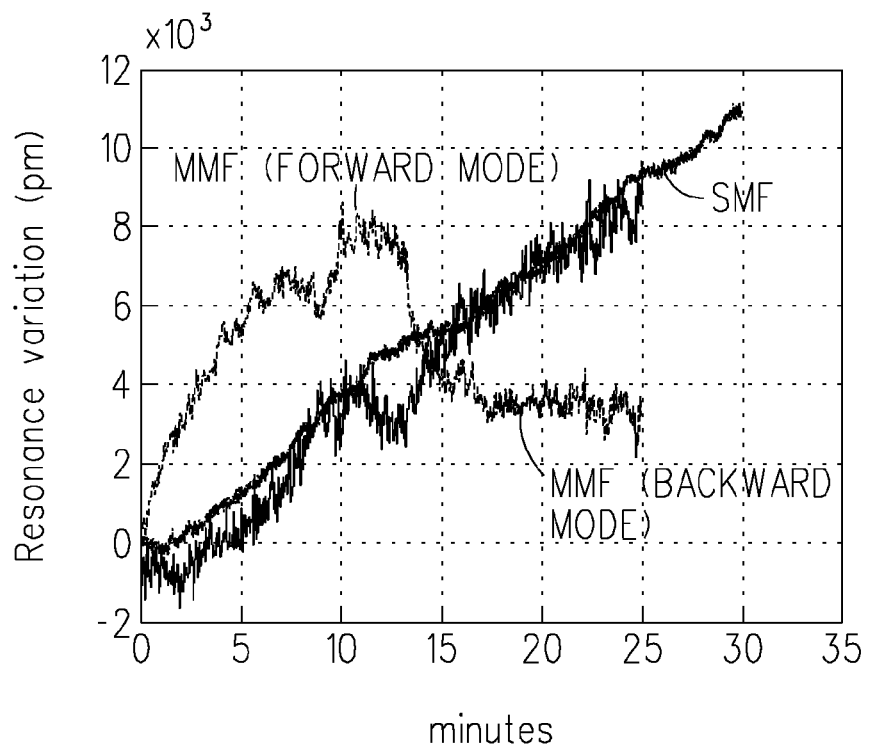
FIG. 12 is a graph that is used to compare resonance wavelength measurements which were made by the optical reader systems shown in FIGS. 2 and 7.
Figure 13:
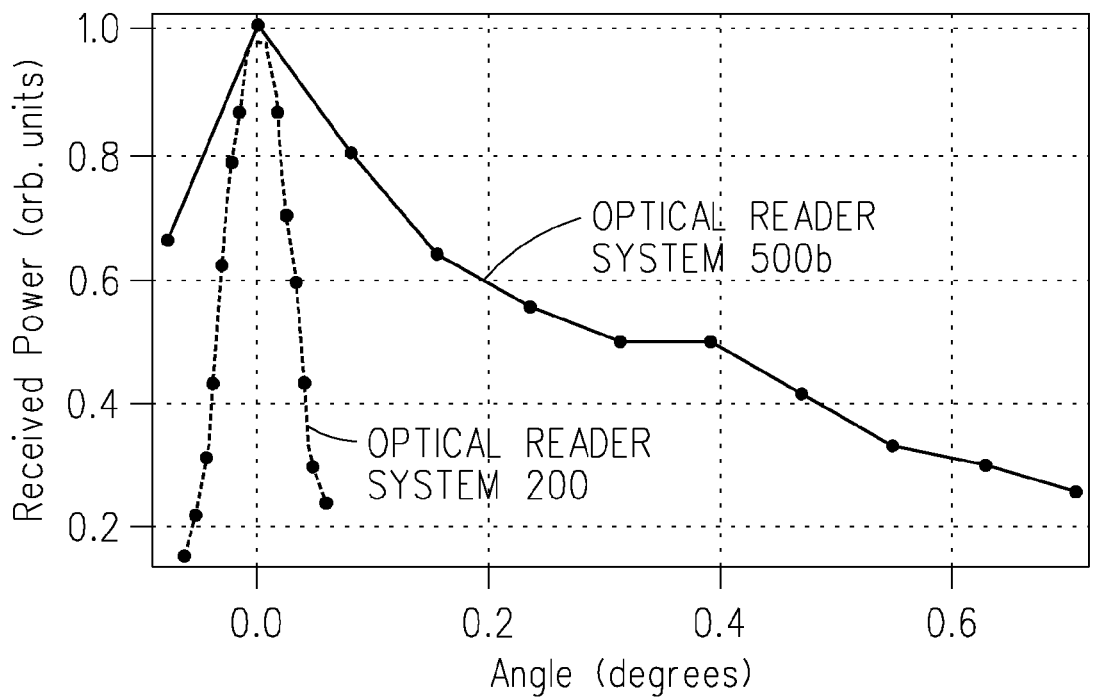
FIG. 13 is a graph that shows the power received vs. incident angle that was measured while testing the optical reader systems shown in FIGS. 2 and 7.

FIG. 12 is a graph that is used to compare the interference in a biosensor's resonance wavelength over 30 minutes that were measured by two optical fiber systems 200 and 500*b* (see FIGS. 2 and 7). The "SMF" curve is the resonance measured by the optical reader system 200. And, the "MMF (forward mode)" and "MMF (backward mode)" indicate the resonances measured by the optical reader system 500*b*. These three curves show that the MMF resonances follow relatively well the SMF resonance measured by the optical reader system 200. However, one can still see some slow fluctuations (especially visible in the MMF forward propagating mode curve) which can be attributed to some residual mode competition in the multimode fiber 704. And, FIG. 13 shows the evolution of the collected power as a function of the angular misalignment of a sensor plate (LID microplate) when using optical reader systems 200 and 500*b*. As can be seen, the angular tolerance is highly relaxed with optical reader system 500*a* as compared to the angular tolerance of optical reader system 200.

In conclusion, the measurements in FIG. 12 indicate that the optical reader system 500*b* with the MMF configuration has a lower resonance stability than the optical reader system 200 which has a SMF configuration. However, in FIG. 13 it can be seen that if the angular deformation of the sensor plate (LID microplate) is such that it would not be possible to use the SMF configured optical reader system 200, then the optical reader system 500*b* may be the best one to use in this situation.

Yet another problem that should be addressed when using the optical reader system 500*b*, is related to angular sensitivity. Indeed, the angular sensitivity of the optical reader system 500*b* is around 0.5 nm/mRd and is an order of magnitude higher than the SMF configuration of optical reader system 200.

To solve the angular sensitivity problem, one possibility is to use a method that was described with respect to another type of optical reader system that was disclosed U.S. patent application Ser. No. 10/676,352 entitled "Double Resonance Interrogation of Grating-Coupled Waveguides". This method involves the measurement of the backward and forward propagating modes and then the calculation of the average of both. The average is, in first approximation, insensitive to the angles. For a more detailed description about this method, reference is made to this patent application, the contents of which are incorporated by reference herein.

Figure 14:
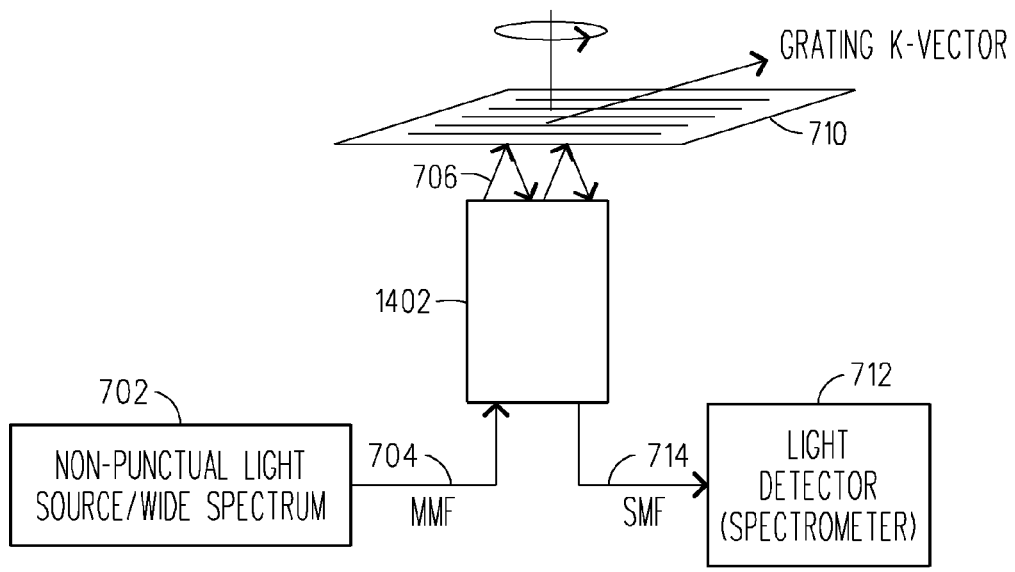
FIG. 14 is a diagram that shows how a dual fiber collimator of the optical reader system shown in FIG. 7 can be oriented to interrogate a biosensor at a normal incidence.

A second approach which can be used to solve the angular sensitivity problem, is to interrogate the biosensor 710 close to normal incidence. In this case, the biosensor 710 is not in its linear regime anymore and the variation of the resonance wavelength as a function of the incidence angle θ becomes close to zero. FIG. 14 shows how to adjust a dual fiber collimator 1402 (which contains fibers 704, 714 and the collimating lens 708). Basically, one angularly adjusts the biosensor 710 around the vertical axis (clocking) to have the pointing-vector of the incident light beam 706 perpendicular to the grating k-vector of the biosensor 710 so the biosensor 710 can be interrogated at a normal incidence.

Figure 15:
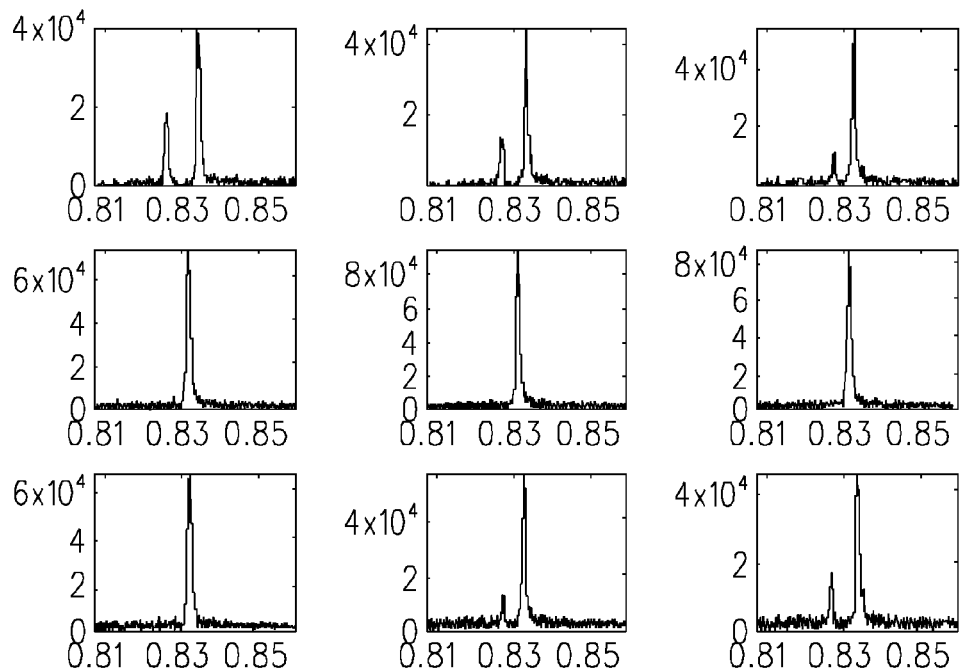
FIG. 15 illustrates plots obtained when the optical reader system shown in FIG. 7 was used to interrogate a biosensor at a normal incidence.
Figure 16A:
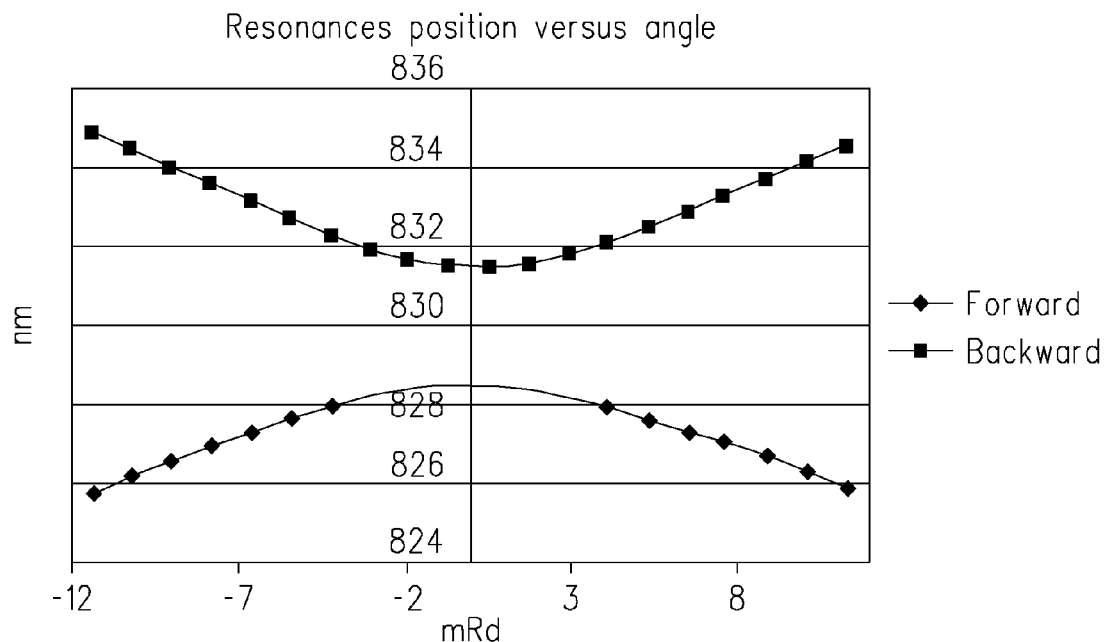
FIGS. 16A and 16B are two graphs which show the position and peak power of the resonant peaks shown in the plots of FIG. 15.
Figure 16B:
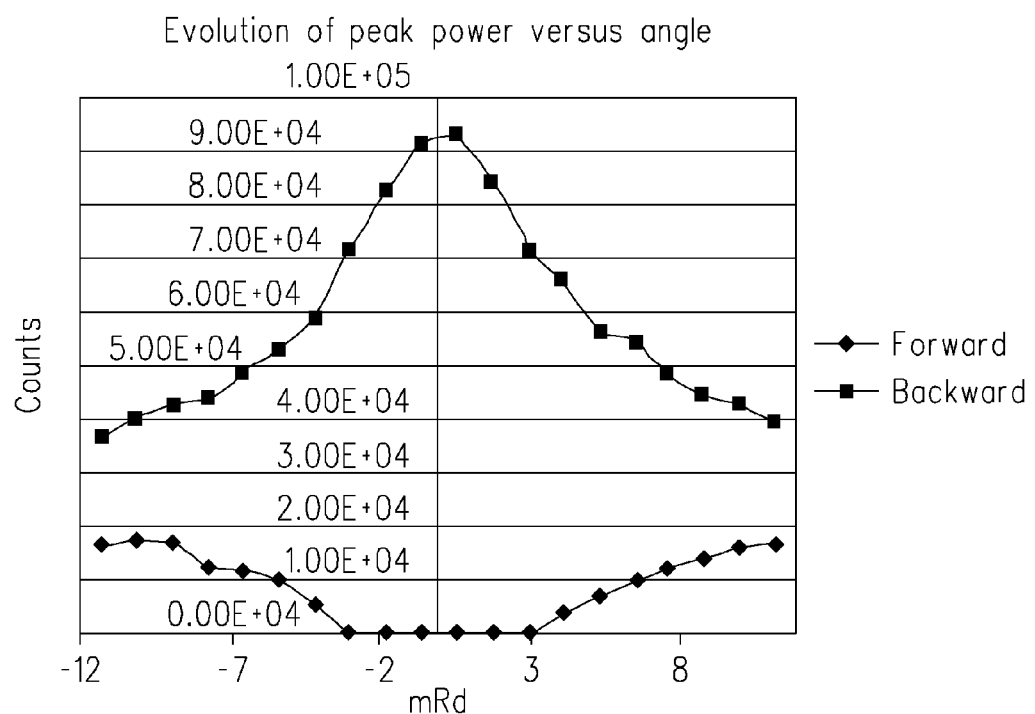

To experimentally validate this configuration, the aforementioned exemplary optical reader system 500*b* was used to interrogate the biosensor 710 at near normal incidence. This allowed one to vary the sensor angle over a wide range while still being able to collect a substantial fraction of the reflected resonant light. FIG. 15 illustrates plots that where obtained from this experiment which show the evolution of the resonance as a function of the tilt of the sensor plate (or biosensor 710) for an angle from −11 mRd to +11 mRd. As can be seen, when one comes close to the normal incidence, the peak power of the forward resonance (peak on the left) decreases but remains constantly separated from the backward resonance by a finite amount (peak on the right). Next, FIGS. 16A and 16B illustrate two graphs which indicate the position and peak power of the two resonant peaks shown in FIG. 15. As can be seen, the function in these graphs is close to being a hyperbole, where the slope being zero at normal incidence. As can also be seen, another advantage of using the optical reader system 500*b* configured in this way is that the reflectivity of the backward propagating mode gets highly increased.

Figure 17:
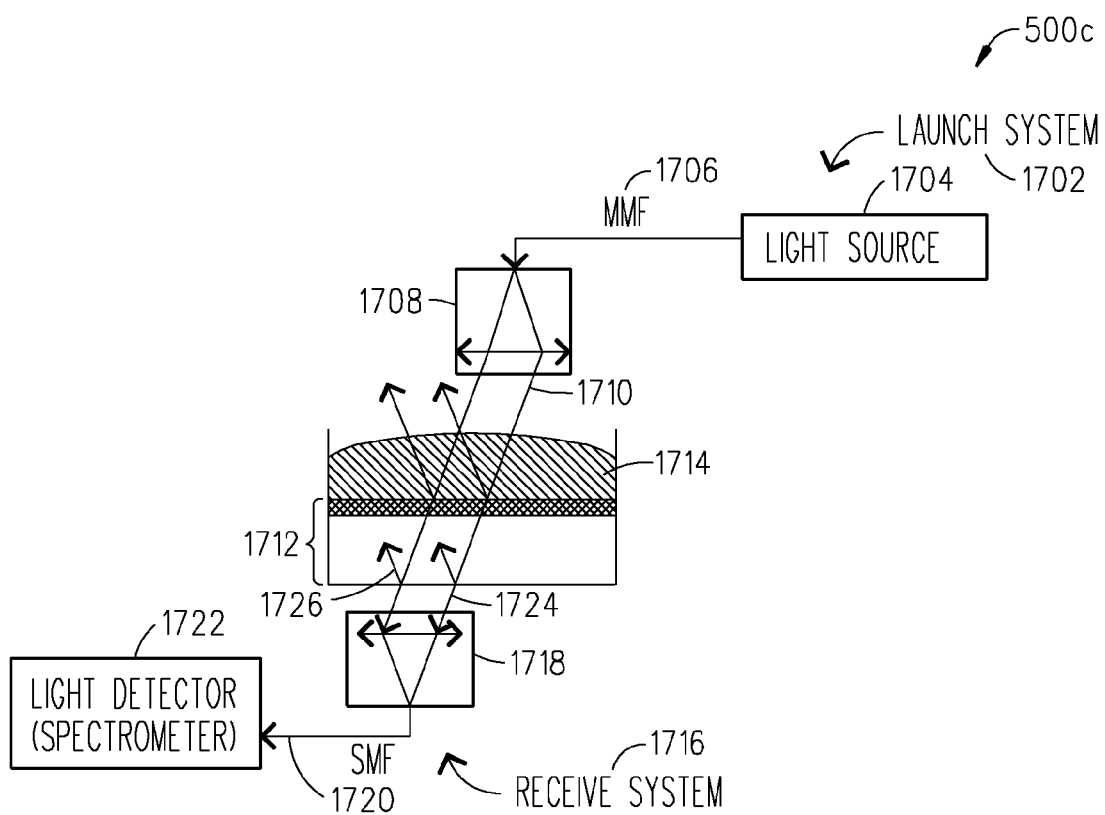
FIG. 17 is a block diagram that illustrates an optical reader system in accordance with a third embodiment of the present invention.
Figure 18:
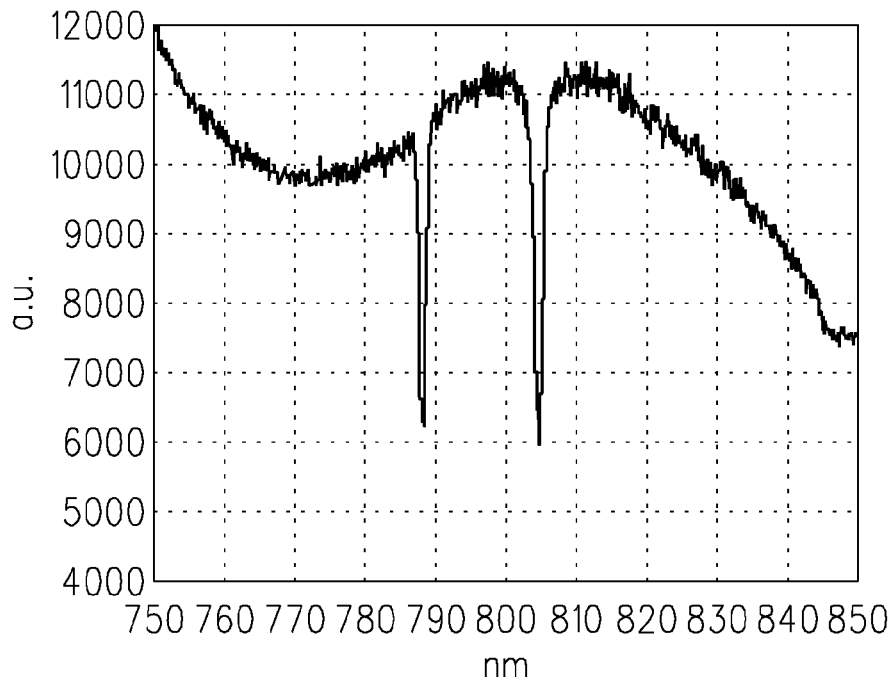
FIG. 18 is a graph that shows a resonance spectrum that was acquired while testing the optical reader system shown in FIG. 17.

Referring to FIG. 17, there is illustrated a diagram of an optical reader system 500*c* which has a transmission measurement configuration in accordance with a third embodiment of the present invention. As shown, the optical reader system 500*c* has a launch system 1702 that includes a light source 1704 (white light source 1704), a multimode fiber 1706 and a collimating lens 1708. The launch system 1702 directs a diverging light beam 1710 to the biosensor 1712. The use of a diverging light beam 1710 means that the light deviation which is generated by the curved surface of liquid 1714 on top of the biosensor 1712 does not matter. In addition, the optical reader system 500*c* has a receive system 1716 that includes a collimating lens 1718, a single mode fiber 1720 and a light detector 1722 (e.g., spectrometer 1722). The receive system 1716 collects a light beam 1724 that passed through the biosensor 1712. An advantage of the transmission measurement configuration is that parasitic reflections 1726 that happen on the back face of the biosensor 1712 are reflected upwards and not collected by the receive system 1716. FIG. 18 is a graph that shows the resonance spectrum that was acquired while testing an exemplary optical reader system 500*c*. As can be seen, the backward and forward propagating TM modes in this graph have inverted spectrums.

Figure 19:
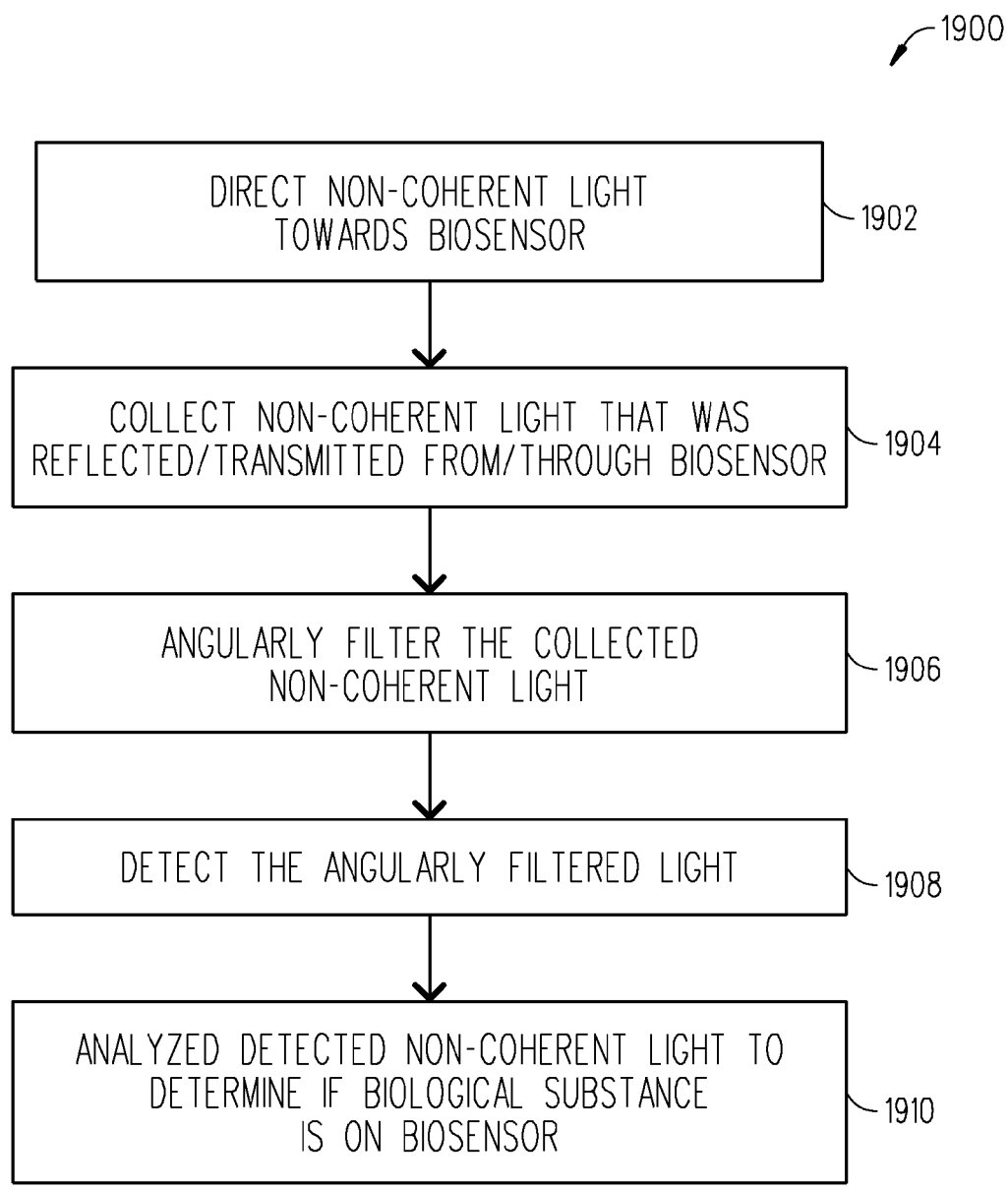
FIG. 19 is a flowchart illustrating the steps of a method for interrogating one or more biosensors in accordance with the present invention.

From the foregoing, it can be readily appreciated by those skilled in the art that the present invention also includes a method 1900 for interrogating a biosensor to determine if a biological substance is located on the biosensor or if a biomolecular event took place on the biosensor. As shown in FIG. 19, the method 1900 includes the steps of: (a) directing a non-coherent light towards a biosensor (step 1902); (b) collecting the non-coherent light that was reflected (or transmitted) by the biosensor (step 1904); (c) angularly filtering the collected non-coherent light (step 1906); (d) detecting the angularly filtered non-coherent light (step 1908); and (e) analyzing the detected non-coherent light to determine if a biological substance is present on the biosensor or if a biomolecular binding event took place on the biosensor (step 1910). Three optical reader systems 500*a*, 500*b* and 500*c* that can implement method 900 have been described above with respect to FIGS. 6, 7 and 17. It should be appreciated that the beams which interface the biosensor are not collimated beams as it may appear in FIGS. 6, 7 and 17. This is because it would be very difficult to illustrate the real shapes of these beams in FIGS. 6, 7, and 17.

Although three embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An optical reader system, comprising:
   a launch system that directs a non-coherent light which is diverging when received by a biosensor; and
   a receive system that collects the non-coherent light from the biosensor where the collected non-coherent light has multiple wavelengths and each wavelength has a specific angle and then the receive system angularly filters the collected non-coherent light such that the angularly filtered non-coherent light has only one specific angle which is detected and the detected angularly filtered non-coherent light has a resonance wavelength which is analyzed to determine if a biological substance is present on the biosensor or if a biomolecular event took place on the biosensor.

2. The optical reader system of claim 1, wherein:
   said launch system includes a free beam propagating non-punctual light source and a collimating lens which are used to direct the non-coherent light which is diverging when received by the biosensor; and
   said receive system includes a beamsplitter which focuses and directs the non-coherent light that was collected from the biosensor to a filtering slit/pin hole which angularly filters the focused non-coherent light such that the angularly filtered non-coherent light can be detected by a light detector and then analyzed by a processor to determine if the biological substance is present on the biosensor or if the biomolecular event took place on the biosensor.

3. The optical reader system of claim 2, wherein said free beam propagating non-punctual light source is a filament or an arc of a lamp.

4. The optical reader system of claim 1, wherein:
   said launch system includes a light source, a multimode fiber and a collimating lens all of which are used to direct the non-coherent light towards the biosensor; and
   said receive system includes a single mode fiber that collects the non-coherent light reflected from the biosensor via the collimating lens and angularly filters the collected non-coherent light such that the angularly filtered non-coherent light can be detected and analyzed to determine if the biological substance is present on the biosensor or if the biomolecular event took place on the biosensor.

5. The optical reader system of claim 4, wherein said multimode fiber is a step index multimode fiber.

6. The optical reader system of claim 4, wherein said launch system further includes a mode scrambler which reduces noise in the non-coherent light that is directed towards the biosensor.

7. The optical reader system of claim 4, wherein said light source is a spatially extended light source which is used to reduce mode competition in the multimode fiber.

8. The optical reader system of claim 4, wherein said launch system and said receive system interrogates the biosensor with the non-coherent light at or substantially close to normal incidence.

9. The optical reader system of claim 4, wherein the angularly filtered non-coherent light that is detected by the light detector is analyzed by measuring both backward and forward propagating modes of a resonance wavelength and then averaging both of those modes to determine if the biological substance is present on the biosensor or if the biomolecular event took place on the biosensor.

10. The optical reader system of claim 4, wherein said non-coherent light that is directed towards the biosensor has a beam divergence that is less than 50 mRd.

11. The optical reader system of claim 1, wherein:
    said launch system includes a light source, a multimode fiber and a collimating lens all of which are used to direct the non-coherent light towards the biosensor; and
    said receive system includes a single mode fiber that collects the non-coherent light transmitted through the biosensor via another collimating lens and angularly filters the collected non-coherent light such that the angularly filtered non-coherent light can be detected and analyzed to determine if the biological substance is present on the biosensor or if the biomolecular event took place on the biosensor.

12. The optical reader system of claim 1, wherein said biosensor is a resonant waveguide grating (RWG) sensor which has a plastic substrate.

13. The optical reader system of claim 1, wherein said biosensor is incorporated within a well of a microplate.

14. A method for interrogating a biosensor, said method comprising the steps of:
    directing a non-coherent light which is diverging when received by a biosensor;
    collecting the non-coherent light from the biosensor, where the collected non-coherent light has multiple wavelengths and each wavelength has a specific angle;
    angularly filtering and the collected non-coherent light such that the angularly filtered non-coherent light has only one specific angle;
    detecting the angularly filtered non-coherent light; and
    analyzing a resonance wavelength of the detected non-coherent light to determine if a biological substance is present on the biosensor or if a biomolecular binding event took place on the biosensor.

15. The method of claim 14, wherein:
    said directing step further includes using a free beam propagating non-punctual light source and a collimating lens to direct the non-coherent light which is diverging when received by the biosensor;
    said collecting step further includes using the collimating lens and a beamsplitter to collect the non-coherent light from the biosensor;
    said angularly filtering step further includes using a filtering slit/pin hole to angularly filter the collected non-coherent light;
    said detecting step further includes using a light detector to detect the angularly filtered non-coherent light; and
    said analyzing step further includes using a processor to analyze the detected non-coherent light to determine if the biological substance is present on the biosensor or if the biomolecular binding event took place on the biosensor.

16. The method of claim 14, wherein:
    said directing step further includes using a light source, a multimode fiber and a collimating lens to direct the non-coherent light towards the biosensor;
    said collecting step further includes using a single mode fiber and the collimating lens to collect the non-coherent light reflected from the biosensor;
    said angularly filtering step further includes using the single mode fiber to angularly filter the collected non-coherent light;
    said detecting step further includes using a light detector to detect the angularly filtered non-coherent light; and
    said analyzing step further includes using a processor to analyze the detected non-coherent light to determine if the biological substance is present on the biosensor or if the biomolecular binding event took place on the biosensor.

17. The method of claim 14, wherein:

said directing step further includes using a light source, a multimode fiber and a collimating lens to direct the non-coherent light towards the biosensor;

said collecting step further includes using a single mode fiber and another collimating lens to collect the non-coherent light transmitted through the biosensor;

said angularly filtering step further includes using the single mode fiber to angularly filter the collected non-coherent light;

said detecting step further includes using a light detector to detect the angularly filtered non-coherent light; and said analyzing step further includes using a processor to analyze the detected non-coherent light to determine if the biological substance is present on the biosensor or if the biomolecular binding event took place on the biosensor.

* * * * *

UNITED STATES PATENT AND TRADEMARK OFFICE
CERTIFICATE OF CORRECTION

PATENT NO. : 7,454,094 B2
APPLICATION NO. : 11/213654
DATED : November 18, 2008
INVENTOR(S) : Jacques Gollier et al.

Page 1 of 1

It is certified that error appears in the above-identified patent and that said Letters Patent is hereby corrected as shown below:

*No.*  *Pg.*  *Line*  *Description*

1    7    1    Strike out: $\lambda = A(neff - \sin \theta)$ and replace with: $\underline{\sin \theta = n_{eff} - \lambda/\Lambda}$.

Signed and Sealed this
Tenth Day of April, 2012

David J. Kappos
*Director of the United States Patent and Trademark Office*